United States Patent
Schoenefeld (10) Patent No.: US 6,981,976 B1
(45) Date of Patent: Jan. 3, 2006

(54) METHOD AND APPARATUS FOR INSERTING AND COUNTERSINKING A MODULAR SCREW

(75) Inventor: Ryan John Schoenefeld, Fort Wayne, IN (US)

(73) Assignee: Biomet, Inc., Warsaw, IN (US)

( * ) Notice: Subject to any disclaimer, the term of this patent is extended or adjusted under 35 U.S.C. 154(b) by 254 days.

(21) Appl. No.: 10/144,186

(22) Filed: May 13, 2002

(51) Int. Cl.
*A61B 17/58* (2006.01)
*A61F 2/00* (2006.01)

(52) U.S. Cl. .................................... 606/104
(58) Field of Classification Search ............. 606/80, 606/86, 96, 99, 104, 167, 180, 73; 81/53.11, 81/53.12, 436, 429, 439, 442
See application file for complete search history.

(56) References Cited

U.S. PATENT DOCUMENTS

| | | | |
|---|---|---|---|
| 2,576,454 A * | 11/1951 | Gearhart ................... 81/442 |
| 3,965,510 A | 6/1976 | Ernst |
| 4,010,737 A | 3/1977 | Vilaghy et al. |
| 4,092,753 A | 6/1978 | Fuhrmann |
| 4,341,206 A | 7/1982 | Perrett et al. |
| 4,651,596 A * | 3/1987 | Rachanski ................ 81/53.2 |
| 5,122,133 A | 6/1992 | Evans |
| 5,190,548 A | 3/1993 | Davis |
| 5,217,486 A | 6/1993 | Rice et al. |
| 5,222,848 A * | 6/1993 | Kuang-Wu .............. 408/239 R |
| 5,431,660 A * | 7/1995 | Burke ..................... 606/104 |
| 5,470,180 A | 11/1995 | Jore |
| 5,549,613 A | 8/1996 | Goble |
| 5,785,468 A | 7/1998 | Peritz |
| 5,980,558 A | 11/1999 | Wiley |
| 6,041,485 A | 3/2000 | Pedlick et al. |
| 6,270,501 B1 | 8/2001 | Freiberg et al. |
| 6,282,998 B1 * | 9/2001 | Beach ...................... 81/437 |
| 2001/0034520 A1 | 10/2001 | Enayati |

* cited by examiner

*Primary Examiner*—Eduardo C. Robert
*Assistant Examiner*—Anu Ramana
(74) *Attorney, Agent, or Firm*—Harness, Dickey & Pierce, P.L.C.

(57) ABSTRACT

An instrument to insert a modular screw into a substrate while allowing for removal of the instrument without disturbing the inserted modular screw. The instrument generally includes a first member that is cannulated. A second member of the instrument engages the modular screw shank. A compression force and locking engagement is created between the modular screw and the instrument which holds the modular screw in the instrument during the insertion of the modular screw. After the modular screw shank has been inserted, the second member of the instrument is removed from the first member which allows for the first member of the instrument to rotate freely around the modular screw. In this way, the instrument can be removed from the modular screw without disturbing the modular screw after implantation.

28 Claims, 5 Drawing Sheets

METHOD AND APPARATUS FOR INSERTING AND COUNTERSINKING A MODULAR SCREW

FIELD OF THE INVENTION

The present invention relates to an instrument to insert a modular screw shank into a structure, and more particularly, to a countersinking instrument that can insert a modular screw shank and be removed without disturbing the inserted modular screw shank.

BACKGROUND OF THE INVENTION

It is generally known in the art to interconnect at least two different elements with a member such as a screw. For example, in medical procedures, a bone plate may be affixed to a fractured or broken bone using a screw which passes through the bone plate and thoroughly engages the substrate bone. In other medical applications, two portions, of fractured bone may be joined together by a screw. The screw generally includes a head portion, which allows a tool to engage the screw, and an integral shank portion, which has threads for engaging the substrate bone. The tool to engage the head portion may be any appropriate tool which can apply enough torque between the tool and the screw to thread it into the substrate.

With these commonly known systems, however, the entire screw is formed of a single material. This single material may be a material that is bio-absorbable. Therefore, after a period of time, the screw will resorb into the body into which it is implanted. Other screws may be formed of materials which are not bio-resorbable and remain permanently affixed within the body into which they are implanted. A bio-resorbable screw, after it has been resorbed, applies no fixation force to an implanted portion or to the bone into which it was implanted. On the other hand, a screw which is formed of a non-resorbable material remains permanently within the bone and may protrude undesirably from the bone into which it is affixed.

It is also known to provide a cannulated screw which includes a cannula through the screw. The cannula in the screw allows it to be guided into the implantation site using a guide system such as a wire. Therefore, the physician, while implanting the screw, does not need to have a clear view of the entire surgical area, but rather may use the wire to guide the screw into place.

It has become desirable to provide a screw which is modular. A modular screw may include a bio-resorbable and a non-bioresorbable portion to be implanted at a single location. Therefore, a non-resorbable portion may always be permanently affixed within the body to provide a fixation in the substrate. While the resorbable portion is resorbed into the body, thereby removing any protrusions which may not be desirable.

The insertion of such a modular screw can be particularly difficult. In particular, a modular screw may include a modular head which is inserted separate from the modular shank portion of the modular screw. Therefore, an instrument to engage such a modular screw requires unique and new characteristics to engage and insert the modular screw. If the modular screw is large enough, protrusions or indentations may be included on the modular screw which may be engaged by an instrument to insert and remove the modular screw. If the modular screw is particularly small, however, there may not be space to form such indentations or protrusions. Therefore, it is desirable to provide an instrument which can insert and remove a modular screw which is small and does not allow for the inclusion of protrusions or detents to be engaged by the instrument.

SUMMARY OF THE INVENTION

The present invention generally provides an instrument to insert a modular screw into a substrate while allowing for removal of the instrument without disturbing the inserted modular screw. The instrument generally includes a first member that is cannulated to receive internally the modular screw. A second member of the instrument engages the modular screw creating a compression force and a locking engagement between the modular screw shank and the instrument, which holds the modular screw in the instrument during the insertion of the modular screw. After the modular screw has been inserted, the second member of the instrument may be removed or loosened from the first member allowing the first member of the instrument to rotate freely around the modular screw. In this way, the instrument can be removed from the modular screw without disturbing the modular screw after implantation.

A first embodiment of the present invention includes an instrument for inserting and removing a modular screw. The instrument includes a cannulated holding member to hold the modular screw. An engagement member movable between an engaged position and a non-engaged position. An engaging system is adapted to direct the engagement member between the engaged position and the non-engaged position. When the engagement member is in the engaged position the modular screw is locked relative the holding member.

A second embodiment of the present invention includes an instrument for inserting a shank of a modular screw into a substrate and countersinking the same. The instrument includes a holding member comprising a first member, that is cannulated, having a first end and a second end. The cannulated member has a first engagement section adjacent the first end and a second engagement section adjacent its second end. An engagement member is movable between an engaged position and a non-engaged position within the cannula of the holding member. The first engagement section is adapted to engage the shank. The second engagement section selectively engages the engagement member. When the engagement member is in the engaged position in the second engagement section, the engaging member holds the shank in a single position relative to the holding member.

A third embodiment includes a system to insert a modular screw a distance into a structure such that the modular screw does not move out of the structure when the system is removed. The system includes a holding member including a first cannulated member having a first end and a second end. An engagement member including a second cannulated member has a first end and a second end, wherein the first end of the engagement member is adapted to be received in the second end of the holding member. A connection mechanism selectively interconnects the holding member and the engagement member. The first end of the holding member is adapted to engage the shank in the cannula. The engagement member engages the shank through the holding member to hold the shank in a single position relative to the holding member. The engagement member, when engaging the shank, is also fixed relative to the holding member.

The present invention presents a new method of manipulating a modular screw shank in relation to a substrate with an instrument. The method includes providing an instrument including a holding member and an engagement member. A modular screw is inserted into a shank end of the holding member. The modular screw is engaged with the engagement member between the holding member and the engaging member such that the modular screw shank is selectively fixed relative to the holding member. A force is transferred to the modular screw via the provided instrument.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses. Although the following description describes inserting a modular screw into a bone it may also be used for other procedures, for example the tool may be used to insert a modular screw through a plate.

Figure 1A:
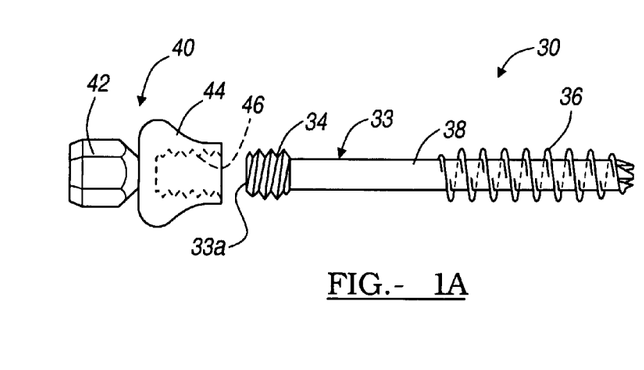
FIG. 1a is an exploded view of a modular screw.
Figure 1B:
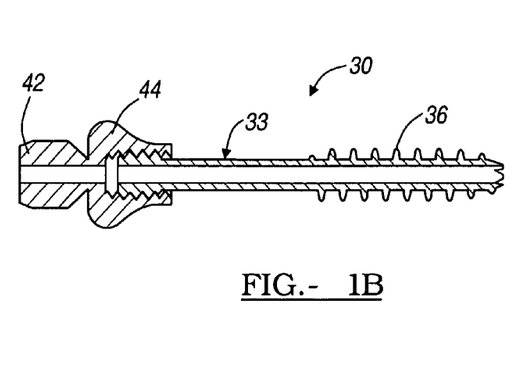
FIG. 1b is a cross-sectional view of an assembled modular screw.

With reference to FIGS. 1a and 1b, a modular screw 30 is illustrated. The modular screw 30 includes a shank portion or a modular shank 33 that has a shank engaging end 33a. At a first end of the screw shank 33, is a set of head engaging threads 34. Substrate engaging threads 36 are on an end opposite the head engaging threads 34. It will be understood that a substrate, such as a bone substrate is often engaged by the substrate engaging threads 36. Furthermore, the substrate engaging threads 36 may be self-tapping and self-drilling. Therefore, the substrate engaging threads 36 do not require a previously drilled and tapped hole. A smooth area 38 separates the head engaging threads 34 and the substrate engaging threads 36. The smooth area 38, however, is not necessary. It will be understood, therefore, that the head engaging threads 34 may extend along the smooth area 38 and meet the substrate engaging threads 36. Otherwise, the smooth area 38 may simply be eliminated and the entire screw shank 33 will simply include head engaging threads 34 or substrate engaging threads 36.

The modular screw 30 also includes a modular head or head portion 40. The head portion 40 includes a drive section 42 and a head section 44. Within the head section 44 are internal head threads 46 which are adapted to engage the head engaging threads 34 on the screw shank 33. In this way, once the modular screw 30 has been inserted into a substrate, the internal head threads 46 engage the head engaging threads 34 for affixing the head section 44 to the shank 33. After this, the drive section 42 may be cut off of the head portion 40 through any appropriate means. The head portion 40 may be formed of a polymer material. The polymer material may be a resorbable material so that after a time the head section 44 is absorbed into the body. For greater detail on a modular screw, U.S. patent application Ser. No. 09/853,425, entitled "Bone Screw Having Bioresorbable Proximal Shaft Portion" is incorporated herein by reference.

Figure 2:
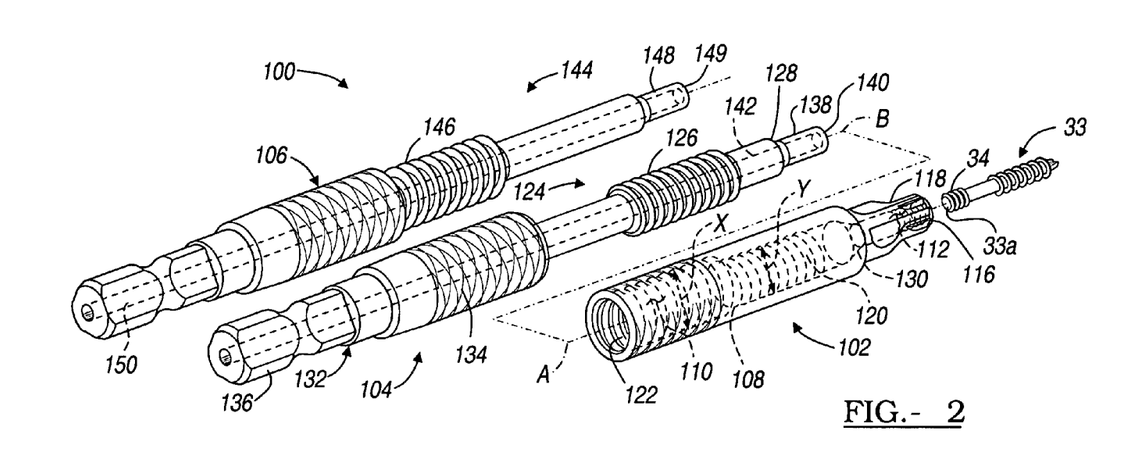
FIG. 2 is an exploded view of a tool to insert and counter sink a modular screw shank according to a first embodiment of the present invention.

In a first embodiment of the present invention illustrated in FIG. 2, a modular screw inserter instrument or tool 100 includes a holding or countersinking section 102 which may be engaged with either an inserting engagement member 104, also known as an inserting locking section, or a removing engagement member 106, also known as a removing locking section. The holding member 102 is a cannulated member defining a cannula 108 extending along a central axis A around which also defines a center of the holding member 102. The cannula 108 has a first cannula section 110 and a second or shank cannula section 112. The shank cannula section 112 has internal shank engaging threads 116 which are adapted to substantially mate with the external head engaging threads 34 of the screw shank 33. Formed externally of the shank cannula section 112 are countersinking flutes 118. The countersinking flutes 118 countersink an area for the head 40 in a substrate during implantation. In the first cannula section 110, extending along axis A and away from the shank cannula section 112, is a second set of threads which are inserting threads 120 and a third set of threads which are removing threads 122. The removing threads 122 are formed axially a distance from the inserting threads 120.

The inserting threads 120 are right hand or clockwise threads which generally are for inserting. That is, the inserting threads 120 are formed in a right hand manner in the first cannula section 110 so as to engage a member having external right hand threads. This allows the holding member 102 to be turned in a clockwise or right hand direction once engaged by the proper member, as described herein. The removing threads 122 are formed in a left hand manner. The removing threads 122 engage external left hand threads allowing the holding member 102 to be turned in a counterclockwise or left hand direction, also described herein. The major diameter Y, or the diameter from a thread peak to a thread peak across from it, of the inserting threads 120 is smaller than the minor diameter X, the diameter from a thread valley to a thread valley across from it of the removing threads 122. This allows the inserting threads 120 and the removing threads 122 to be substantially independent of one another and only mate with a member which has mating threads for one particular set of threads formed in the first cannula section 110. In particular and described further herein, external threads that engage the inserting threads 120 may pass through the removing threads without engaging the removing threads 122.

The inserting engagement member 104 is formed cylindrically and extends along an axis B. A threaded section 124 includes external inserting member threads 126 which mate substantially with the inserting threads 120 in the first cannula section 110. In this way, the inserting engagement member 104 be threaded into the first cannula section 110 by mating the inserting member threads 126, of the threaded section 124, with the inserting threads 120 in the first cannula section 110. This is so because the major diameter of the inserting member threads 126 is less than the minor diameter of the removing threads 122. Therefore, the inserting member threads 126 pass through the removing threads 122.

Because the inserting threads 120 are right hand threads, the inserting member threads 126 are right hand threads. Therefore, as the inserting engagement member 104 is tightened into the first cannula section 110, the inserting engagement member 104 is turned to the right or clockwise. Once the inserting engagement member 104 is locked in placed, as described herein, the tool 100 can then be turned in a clockwise direction. This also turns the screw shank 33 in a clockwise direction driving the screw shank 33 into a substrate, as described herein.

Extending from the threaded section 124 is a manipulation section 132. The manipulation section 132 includes a first manual manipulation section 134. The manual manipulation section 134 may be knurled or otherwise textured to allow for an easy grip of a hand onto the inserting engagement member 104. Extending from the manual manipulation section 134 is an automatic or tool manipulation section 136. The tool manipulation section 136 includes any appropriate design that allows it to be easily inserted into an automatic tool, such as a drill. In this way, the inserting engagement member 104 can be inserted into the holding member 102 using either manual manipulation or automatic manipulation. Additionally, once the engagement member 104 or 106 has been inserted into the holding member 102, the automatic manipulation section 136 is used to affix it to a drill to allow for a greater torque and force during the insertion of the screw shank 33.

Extending from an end opposite the manipulation section 132, but still along axis B, is the shank engagement nose 138. The shank engagement nose 138 has an outer diameter which is substantially equal to the internal diameter defined by the shank engaging threads 116 in the shank cannula section 112. The shank engagement nose 138 includes a leading edge 140 which is designed to mate with the engaging end 33a of the screw shank 33. The diameter of the shank engagement nose 138 may be any appropriate size to engage the engaging end 33a and not necessarily equal to the diameter of the threads. The inserting engagement member 104 may also define an inserting member cannula 142.

The removing engagement member 106 includes a releasing threaded section 144 including external releasing threads 146. The releasing threads 146 are designed to substantially mate with the removing threads 122, formed in the first cannula section 110. Because the removing threads 122 are left hand threads, the removing engagement member 106 is rotated in a counterclockwise direction to insert the removing engagement member 106 into the holding member 102. In this manner, when a leading edge 149 of a screw shank engagement nose 148 engages the engagement end 33a of the screw shank 33, the instrument 100 may be used to remove the screw shank 33 after it has been inserted. The removing engagement member 106 also includes a removing cannula 150. It will be understood that the removing engagement member 106 will also have a manipulation portion 132', similar to the manipulation portion 132 of the inserting engagement member 104, to manipulate the removing engagement member 106, wherein similar portions are denoted with the same numerals augmented by a prime.

Figure 3A:
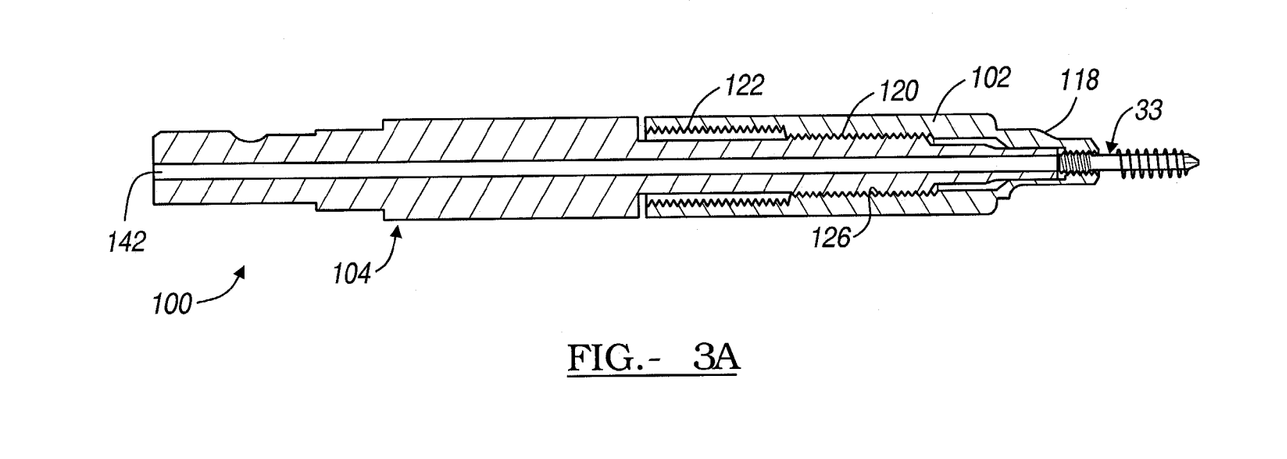
FIG. 3a is a cross sectional view of the assembled tool according to the first embodiment, to insert the modular screw shank.
Figure 3B:
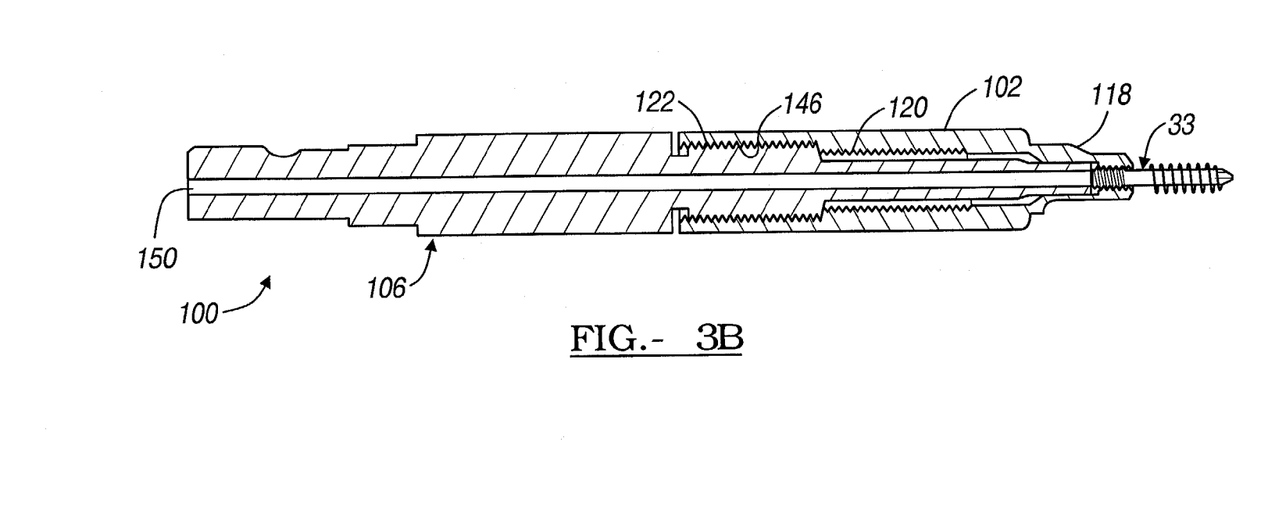
FIG. 3b is a cross sectional view of the assembled tool according to the first embodiment, to remove the modular screw shank.

With reference to FIGS. 3*a*–3*b*, the instrument 100 is illustrated assembled. The inserting engagement member 104 interacts with the inserting threads 120 while the shank 33, interacts with the internal shank engaging threads 116 to form an engagement system. The inserting engagement member 104 has been fully inserted into the holding member 102. It will be understood, however, the following process also generally applies if the removing engagement member 106 is inserted in the holding member 102, as specifically illustrated in FIG. 3*b*. The screw shank 33 is first inserted into the holding member 102, by engaging the head engaging threads 34 of screw shank 33 with internal shank engaging threads 116 of the holding member 102 to define a first engagement section. The inserting engagement member 104 is then inserted into the cannula 108 of the holding member 102 to engage the screw shank 33 which defines a second engagement section. The leading edge 140 of the shank engagement nose 138 presses against the engaging end 33*a* of the screw shank 33 and holds the screw shank 33 in place with a friction force. The two engagement sections create this engagement system.

The force of the inserting engagement member 104 pushes against the engaging end 33*a* of the screw shank 33 to hold it in place. When the screw shank 33 is so held it is locked. When locked the instrument 100 can be operated to insert the screw shank 33 into a bone or other substrate. The pressure of the shank engagement nose 138 not only holds the screw shank 33 in place, but holds the inserting engagement member 104 in place relative to the holding member 102. This allows for the inserting engagement member 104 to be the impetus of all the force applied to the screw shank 33 and the countersink flutes 118. The inserting engagement member 104, when the shank engagement nose 138 engages the screw shank 33, is locked in place relative to the holding member 102.

Once the instrument 100 is fully assembled, by placing the screw shank 33 in the shank engaging threads 116 and then locking the screw shank 33 in place with the inserting engagement member 104, the screw shank 33 may be inserted into a bone 200. With reference to FIGS. 4 through 7*b*, the method of using the tool 100 to insert a screw shank 33 into the bone 200 is more fully described. After locating and properly preparing the bone 200, which has a malady such as a crack 202, the insertion of the screw shank 33 may begin. It will be understood that the bone 200 is generally surrounded by other soft tissue masses which are not illustrated for clarity.

Figure 4:
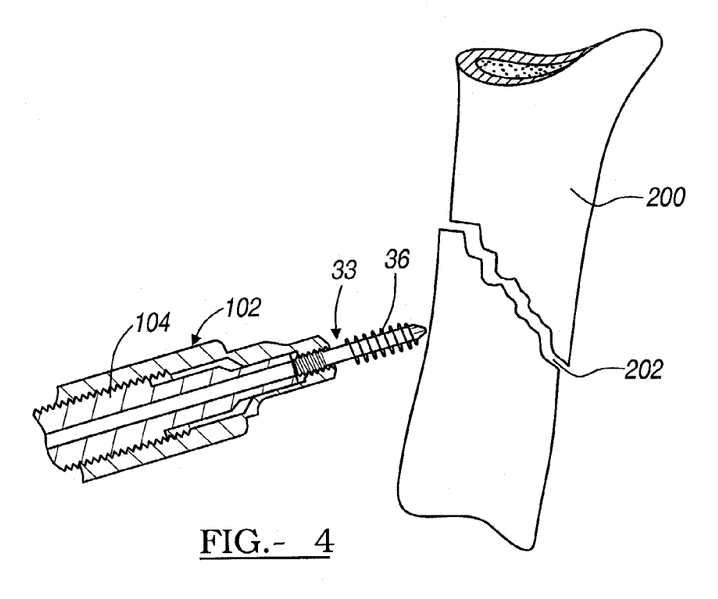
FIG. 4 is a partial detailed cross-section of the tool including a modular screw shank preparing to insert the shank into a bone.

The screw shank 33 is inserted into the holding member 102 such that the head engaging threads 34 of the screw shank 33 engage the internal shank engaging threads 116 of the holding member 102. The inserting engagement member 104 is then threaded into the holding member 102, through the interaction of the inserting member threads 126 and the inserting threads 120. The leading edge 140 of the shank engagement nose 138 abuts the screw shank 33. After the locking force is created between the leading edge 140 of the shank engagement nose 138 and the engaging end 33a of the shank 33, the screw shank 33 is locked in place relative to the holding member 102. The locking force also locks the inserting engagement member 104 relative to the holding member 102.

It will be understood that the portion of the screw shank 33 extending from the holding member 102 may be any appropriate length. In particular, the length of the screw shank 33 extending from the holding member 102 is sufficient to engage the substrate bone 200 in any appropriate manner. Such as illustrated where the screw shank 33 extends into the bone 200 to engage the bone 200 on both sides of the crack 202. The portion of the screw shank 33 within the holding member 102 is not threaded into the bone 200 with the tool 100. The screw shank engagement nose 138 may also be any appropriate length so that it will engage the screw shank 33 while allowing an appropriate amount of the screw shank 33 to extend from the holding member 102.

The screw shank 33 may be self drilling and self tapping screw, so that it acts as a drill bit and tap bit. Therefore, once the inserting engagement member 104 has been locked onto the screw shank 33, the entire tool 100 is engaged in any other appropriate instrument or tool to provide the power and torque to drill the screw shank 33 into the bone 200. As the tool 100 is inserted further into the bone 200, the countersinking flutes 118 also form a countersink area 204 in the bone 200. As specifically illustrated in FIG. 6, when the tool 100 is removed, the screw shank 33 is inserted into the bone 200 and a countersink area 204 remains.

Figure 5:
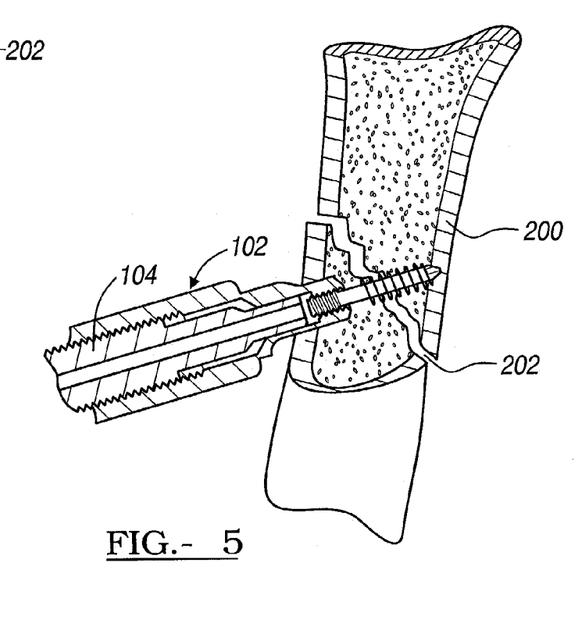
FIG. 5 is a partial detailed cross-section of the tool including a modular screw shank being inserted into a bone.

With reference to FIG. 5, once the screw shank 33 has been inserted a sufficient distance into the bone 200, the screw shank 33 engages both sides of the crack 202 to hold the bone 200 in the proper orientation to allow healing. Once the screw shank 33 has been inserted the appropriate distance, the inserting engagement member 104 may be removed or loosened from the holding member 102 by turning the inserting engagement member 104 in a counter clockwise direction. This leaves the holding member 102 in position. Once the inserting engagement member 104 has been removed or loosened, the holding member 102 may rotate substantially freely about the screw shank 33. Although the remaining discussion refers to removing the engagement members, this is only for clarity and simply loosening them provides equal advantages. The forces between the screw shank 33 and the bone 200 are now greater, after removing inserting engagement member 104, than the forces now between the screw shank 33 and the shank engaging threads 116. Therefore, the holding member 102 is removed from the screw shank 33 by unscrewing the holding member 102. Simply unscrewing the holding member 102 leaves only the screw shank 33 in place in the bone 200.

Figure 6:
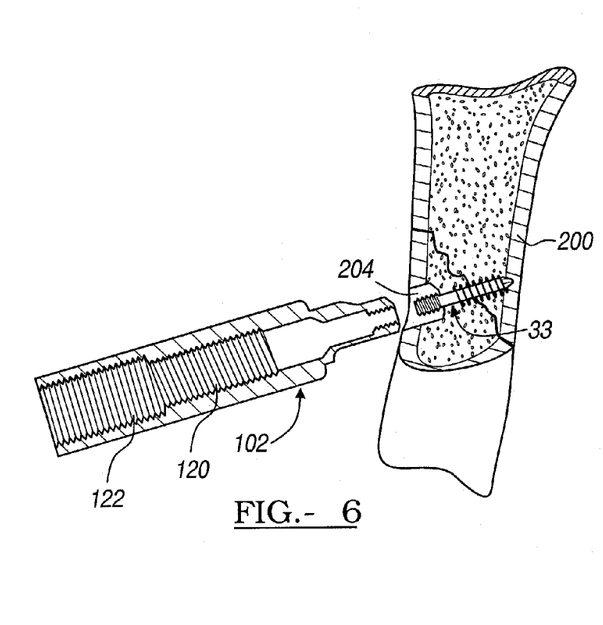
FIG. 6 is a partial cross section detailed view of a tool after inserting the modular screw shank and removing the instrument.

As shown particularly in FIG. 6, the screw shank 33 extends into the countersink area 204 the distance that the screw shank 33 was inside the holding member 102. The screw shank 33, however, is left unmoved from its inserted position due to the fact that the inserting engagement member 104 had been removed from a holding member 102. Removing the inserting engagement member 104 from the holding member 102 substantially eliminates the locking force between the shank 33 and the shank engaging threads 116. Removing the locking force unlocks the tool 100 allowing the holding member 102 to be easily removed from the screw shank 33. Furthermore, this leaves the screw shank 33 in place and appropriately placed in the countersink area 204 and the bone 200.

Figure 7A:
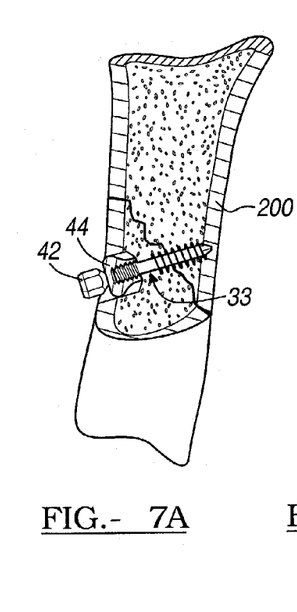
FIG. 7a is a partial detailed view illustrating the screw shank inserted including a modular head and undisturbed by removing the instrument.
Figure 7B:
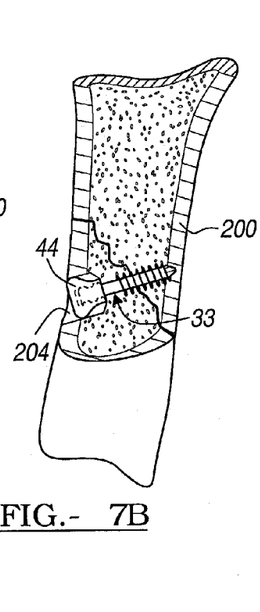
FIG. 7b is a partial detailed view illustrating the screw shank inserted including a modular head with the modular head manipulation section removed.

After the holding member 102 has been removed, any appropriate modular screw head 40 may be affixed to the modular screw shank 33. One appropriate modular screw head is disclosed in U.S. application Ser. No. 09/853,425 entitled "Bone Screw Having Bioresorbable Proximal Shaft Portion" incorporated herein by reference. The modular screw head section 44 fits within the countersink area 204 produced in the bone 200 by the countersinking flutes 118. This allows for a substantially flush fit of the head section 44 with the bone 200 to aid in healing. In addition, the head section 44 may be formed of a resorbable material so that after a period of time it will be resorbed into the body. Bone 200 may then regrow into the countersink area 204 so that no foreign or implant material is actually exterior of the bone 200. In this way irritation between the implant and the soft tissue, which will grow over the bone 200, is substantially reduced.

If at a certain point the screw shank 33 is desired to be removed from the bone 200, such as to reset or move the screw shank 33, the removing engagement member 106 is employed. If the head section 44 is present, it is first removed so that the shank engaging threads 116 may engage the head engaging threads 34 of the screw shank 33 by threading the holding member 102 onto the screw shank 33, defining a first engagement section. After this has occurred, the removing engagement member 106 is threaded into the holding member 102 such that the releasing threads 146 engage the removing threads 122 and form a second engagement section. These two engagement sections define an engagement system of the tool 100.

Because the removing threads 122 are formed in a left hand manner, the removing engagement member 106 is rotated in a counter clockwise direction to mate the releasing threads 146 with the removing threads 122. As the removing engagement member 106 is threaded into the holding member 102, the leading end 149 of the shank engagement nose 148 engages the end 33a of the screw shank 33. As before, a locking force is created by pressing a leading end 149 against the engaging end 33a of the screw shank 33. Once the locking force has been created, the tool 100 may be rotated in a counter clockwise direction to release and remove the screw shank 33.

Once the screw shank 33 is removed or released an appropriate amount from the bone 200, the removing engagement member 106 is unscrewed from the holding member 102 by rotating the removing engagement member 106 in a clockwise direction. This removes or substantially eliminates the locking force so that the screw shank 33 may be rotated freely within the holding member 102. In this way, the screw shank 33 may be removed from the bone 200 after implantation into the bone 200.

It will also be understood that the inserting engagement member 104 and the removing engagement member 106 may be cannulated to provide a passage therethrough. The screw shank 33 may also be cannulated so that an internal passage is formed throughout the entire tool 100 after it is assembled. In this way, a guide wire or other instrument, inserted through the screw shank 33 and through the tool 100, may be used as a guide to guide the screw shank 33 into place.

It will also be understood that the engagement system need not be two separate and distinct portions. In particular, the shank engagement nose 138, 148 may include external threads which have a same diameter and pitch as the head engaging threads 34 on the modular screw shank 33. In this circumstance, only one set of internal threads would be required in the holding member 102 to engage both the modular screw 33 and the engagement members 104 or 106. Therefore, a modification, such as this, does not stray from the scope of the present invention.

Figure 8:
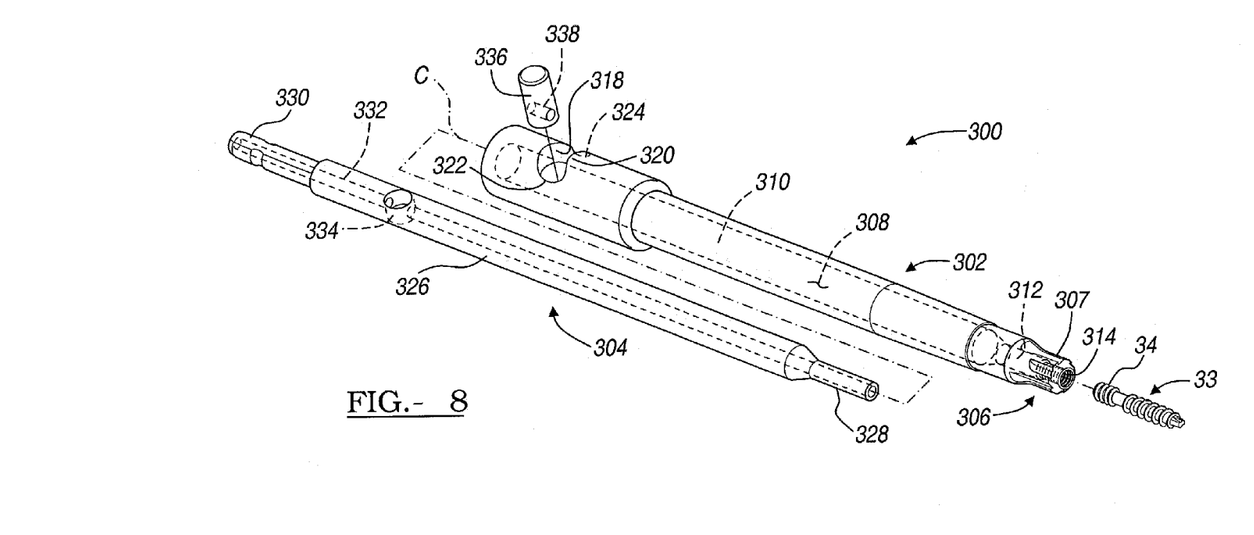
FIG. 8 is an exploded view of a tool to insert a modular screw shank according to a second embodiment of the present invention.
Figure 9:
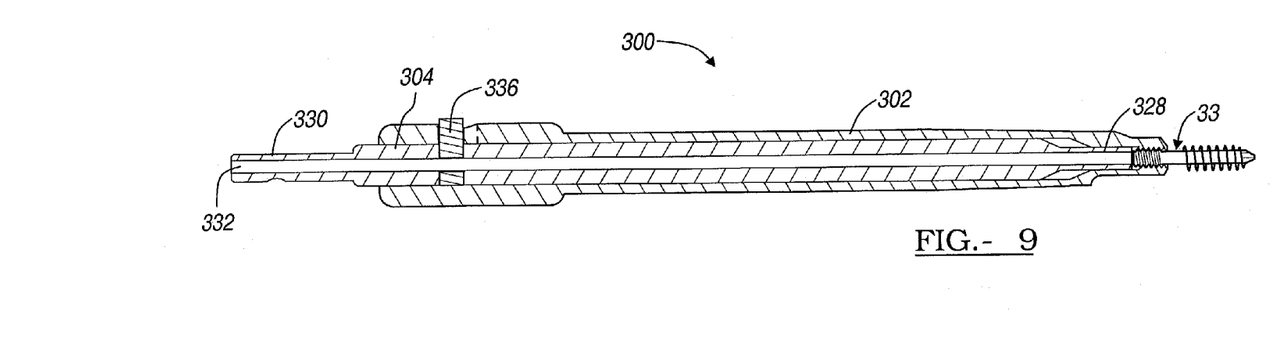
FIG. 9 is a cross-sectional view of the tool to insert a modular screw shank according to the second embodiment of the present invention.

With reference to FIGS. 8 and 9, a second embodiment of the modular screw inserter instrument or tool 300 includes a holding member 302 and an engaging member 304. The holding member 302 includes a first end 306, which has countersinking flutes 307 defined on the exterior thereof. The holding member 302 is formed along an axis C and includes a cannula 308. The cannula 308 includes a first cannula section 310 and a second cannula section 312. The second cannula section 312 has an internal diameter which includes shank engaging threads 314. The shank engaging threads 314 engage the head engaging threads 34 of a modular screw shank 33. In this way, the screw shank 33 may be inserted into the second cannula section 312 for insertion into a substrate.

Formed on an end of the holding member 302, opposite the first end 306 is a track 318. The track 318 defines a bore which includes a central peaked section 320, a clockwise depression 322, and a counter-clockwise depression 324. The track 318 generally defines a C-shape. As described herein, however, the precise shape of the track 318 may be any appropriate shape to provide the mechanism of driving the engagement member 304 into engagement with the screw shank 33.

The engagement member 304 includes a body portion 326 having a screw shank engagement nose 328 extending from one end and a tool engaging section 330 extending from an end opposite the shank engagement nose 328. Formed axially along the engagement member 304, through the nose 328, the body 326, and the tool engaging section 330, is a cannula 332. A bore 334 is formed in the body section 326 of the engagement member 304. The bore 334 receives a pin 336. The pin 336 includes a bore 338 which, when inserted into the bore 334, is substantially axial with the cannula 332 formed in the engagement member 304. This is so that the pin 336 does not obstruct the cannula 332 of the engagement member 304.

With reference to FIG. 9, the tool 300 is assembled and includes the body portion 326 substantially within the first cannula section 310 of the holding member 302. Also, when assembled the shank engagement nose 328 is received substantially in the second cannula section 312. Once the engagement member 304 is received within the holding member 302, the pin 336 is inserted through the track 318 and then into the bore 334, of the engagement member 304 which defines the second engagement section. It will be understood, however, that the pin 336 may also be placed on a biasing spring within the bore 334. With a biasing spring, the pin 336 would spring up through the track 318 rather than being inserted through the track 318. Also, if a biasing spring were used, the track 318 would not need to be a bore, but rather a depression on the inside of the holding member 302. In either case once the pin 336 is inserted into the track 318, the tool 300 is preferably designed to not be disassembled, as described in the first embodiment. Nevertheless, the engagement member 304 is able to move substantially freely within the cannula 108 of the holding member 302.

The operation of the tool 300, according to the second embodiment, will now be more clearly described. Once the tool 300 is fully assembled, a screw shank 33 is threaded into the shank engaging threads 314 defining the second engagement section. This is performed when the engagement member 304 is in a non-engagement position. The non-engagement position is achieved when the pin 336 is substantially axial with the peak 320 of the track 318. Once the screw shank 33 is inserted into the shank engaging threads 314, such that the screw shank 33 substantially meets the shank engagement nose 138 of the engagement member 304, the tool engaging section 330 is engaged in a tool.

To insert the screw shank 33, the tool 300 is turned in a clockwise direction. As the tool 300 is turned in a clockwise direction, the pin 336 rides in the track 318 to engage the clockwise depression 322. The engagement in the clockwise depression 322 forces the engagement member 304 onto the end of the screw shank 33. This substantially locks the screw shank 33 in place within the holding member 302. Therefore, the screw shank 33 may be driven into a substrate, such as a bone, as described in relation to the first embodiment.

Once the screw shank 33 has been inserted to the appropriate depth and the countersink has been cut with the countersink flutes 307, the engagement member 304 is moved to the non-engaging position. That is, the engagement member 304 is rotated, without rotating the holding member 302, so that the pin 336 is substantially axial with the peak 320. At this point, the shank engagement nose 328 no longer engages the screw shank 33. This unlocks the engagement member 304 from the screw shank 33 so that the holding member 302 may be turned freely relative to the screw shank 33. In this way, the tool 300 may be removed from the screw shank 33 without moving the screw shank 33 after it has been inserted into a substrate.

According to the second embodiment of the tool 300, a separate engagement member is not needed to remove a screw shank 33 from a bone. Once a screw shank 33 is inserted into a bone, the holding member 302 is simply threaded over the head engaging threads 34 with the shank engaging threads 314. Once threaded over the screw shank 33, such that the shank engagement nose 328 has engaged the screw shank 33, the tool engaging section 330 is engaged in a power tool. To remove the screw shank 33, the tool 300 is turned in the counter-clockwise direction. Now, the pin 336 travels in the track 318 to engage the counter-clockwise depression 324. The shank engagement nose 328, by this, is moved into an engaged position and engages the screw shank 33. In the engaged position, the engagement member 304 holds the screw shank 33 in a substantially locked position when the pin 336 is in the counter-clockwise depression 324. In this way, the screw shank 33 may be removed from the substrate since the screw shank 33 is locked in position. Then, once the screw shank 33 has been removed, the engagement member 304 is simply moved to the non-engaging position, that is when the pin is substantially axial with the peak 320, and the screw shank 33 may spin freely and removed from the holding member 302.

It is understood that the engaging position provides the locking force between the engagement member 304 and the screw shank 33. According to the second embodiment, rather than screwing the engagement member 304 into the holding member 302, the interaction between the pin 336 and the track 318 provides the locking force. Likewise, the non-engagement position substantially removes the locking force and unlocks the tool 300.

The track 318 may be any appropriate shape to provide the same mechanism as the C-shape of the illustrated track 318. A C-shape is simply one example of an appropriate shape. A track simply needs to be provided to allow the pin 336 to force the engagement member 304 against the shank 33.

The above embodiments are merely examples of tools for inserting and removing a modular screw shank from a substrate such as a bone. It will be understood that other appropriate designs may be used to form a means for inserting and removing a modular screw. In particular, designs similar to retractable pens may be used. In a first position, the retractable pen forces the point out of the body. Similarly, the mechanism, in a first position, forces an internal engagement member towards a modular screw shank to provide a compression or locking force between the modular screw shank and the holding member. The locking force locks the engagement member relative to the screw shank and the holding member. In the locked position, the entire tool may be rotated to either insert or remove the modular screw shank.

The engagement member then also has a non-engaging position, such as when a retractable pen is retracted to retract the point into the body, so that the locking force is removed. When the locking force is removed, the holding member may be removed from the screw shank or the screw shank removed from the holding member. Therefore, it is understood that the above embodiments are simply exemplary of embodiments which may be designed to provide a tool to insert and remove a modular screw shank.

The tool 100, 300 preferably has a member that allows the release of a locking force between the screw shank, which is insertable into a substrate, and the tool itself, so that the tool may be removed from the screw shank without moving the screw shank relative the substrate. In particular, if the forces between the tool and the screw shank were not relieved before removing the tool from the screw shank, then the screw shank would be loosened by removing the tool. In providing an apparatus that allows the substantial elimination of the forces between the tool and the screw shank, the tool may be removed from the screw shank without moving the screw shank once it has been inserted into a substrate. Therefore, a precise and predetermined depth of insertion of the screw shank into a substrate can be achieved. Furthermore, this can be achieved without providing on the screw shank any other engagement mechanism beside external threads. That being that the locking force created between the screw shank and the tool, particularly the internal threads of the holding member and the engagement member, provide the resistance necessary to torque the screw into a substrate. These forces, however, are easily removed by removing the engagement member from the holding member so that the holding member may then be removed from the screw shank without upsetting the placement of the screw shank. Furthermore, this apparatus allows for a headless screw shank to be removed from a substrate after insertion by recreating the locking forces by placing the engagement member within the holding member.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An instrument for inserting and removing a modular screw shank, said instrument comprising:
   a holding member operable to hold the modular screw shank;
   an engagement member movable between an engaged position and a non-engaged position; and
   an engagement system adapted to direct said engagement member between said engaged position and said non-engaged position;
   wherein when said engagement member is in said engaged position the modular screw shank is locked relative said holding member;
   wherein said holding member comprises a cannulated member having a first end and a second end;
   wherein said engagement system is positioned in said first end of said cannulated member;
   wherein said engagement system holds the shank; and
   wherein said engagement system further holds said engagement member and directs and said engagement member in contact with the shank.

2. The instrument of claim 1, wherein said engagement system is a set of cannula threads formed in a cannula of said cannulated member;
   wherein said engagement member includes a set of engagement threads adapted to mate with said cannula threads; and
   wherein said cannula threads are adapted to mate with an external thread of the shank.

3. An instrument for inserting a modular screw shank into a substrate and countersinking the same, the instrument comprising:
   a holding member including a first holding member having a first end and a second end;
   a first engagement section adjacent said first end; and
   a second engagement section adjacent said second end; and
   an engagement member movable between an engaged position and a non-engaged position within said holding member;
   wherein said first engagement section is adapted to engage the shank;
   wherein said second engagement section selectively engages said engagement member;
   wherein when said second engagement member is in said engaged position, in said second engagement section, said engaging member holds said shank in a single position relative to said holding member;
   wherein said second engagement section includes:
      a right hand set of threads formed on the interior of said holding member and adapted to engage a right hand set of engagement member threads; and
      a left hand set of threads formed on the interior of said holding member and adapted to engage a left hand set of engagement member threads;
      wherein either said right hand set of threads or said left hand set of threads are separately and selectively engageable.

4. The instrument of claim 3, wherein said first engagement section includes shank threads formed internally in said holding member, wherein said shank threads are adapted to mate with threads formed on an exterior of the shank.

5. The instrument of claim 3, wherein said engagement member includes said right hand set of engagement member threads and when said engagement member is engaged in said right hand set of threads the shank is able to be inserted into the substrate.

6. The instrument of claim 3, wherein said engagement member includes said left hand set of engagement member threads and when said engagement member is engaged in said left hand set of threads the shank is able to be removed from the substrate.

7. The instrument of claim 3, wherein said second engagement section includes a right hand set of threads formed on the interior of said cannula member and adapted to engage a right hand set of threads formed on said engagement member.

8. The instrument of claim 7, wherein when said engagement member is engaged in said right hand set of threads the shank is able to be inserted into the substrate.

9. The instrument of claim 3, wherein said second engagement section includes a left hand set of threads formed on the interior of said holding member and are adapted to engage a left hand set of threads formed on said engagement member.

10. The instrument of claim 9, wherein when said engagement member is engaged in said left hand set of threads the shank is able to be removed from the substrate.

11. The instrument of claim 3, wherein said second engagement section includes an inserting set of threads and a removing set of threads;
    wherein said engagement member includes an inserting engagement member and a removing engagement member;
    wherein said inserting engagement member includes a thread adapted to be threaded into said inserting set of threads to insert the shank; and
    wherein said removing engagement member includes a thread adapted to be threaded into said removing set of threads to remove the shank.

12. A system to insert a modular screw shank a distance into a structure such that the shank does not move out of the structure when the system is removed, the system comprising:
    a holding member including a first cannulated member having a first end and a second end;
    an engagement member including a second cannulated member having a first end and a second end, wherein said first end of said engagement member is adapted to be received in said second end of said holding member; and
    an engagement section for selectively interconnecting said holding member and said engagement member;
    wherein said first end of said holding member is adapted to engage the shank in said cannula;
    wherein said engagement member engages the shank through said holding member to hold said shank in a single position relative to said holding member;
    wherein said engagement member, when engaging the shank is also fixed relative said holding member;
    wherein said engagement member, when engaging the shank, is also fixed relative said holding member;
    wherein said engagement section includes:
        a right hand set of threads formed on the interior of said cannula member and adapted to engage a right hand set of engagement member threads; and
        a left hand set of threads formed on the interior of said cannula member and adapted to engage a left hand set of engagement member threads;
        wherein either said right hand set of threads or said left hand set of threads are separately and selectively engageable.

13. The system of claim 12, wherein said engagement member includes said right hand set of member threads and when said engagement member is engaged in said right hand set of threads the shank is able to be inserted into the substrate.

14. The system of claim 12, wherein said engagement member includes said left hand set of member threads and when said engagement member is engaged in said left hand set of threads the shank is able to be removed from the substrate.

15. The system of claim 12, wherein said engagement section comprises a right hand set of threads formed on the interior of said holding member and adapted to engage a right hand set of threads formed on said engagement member.

16. The system of claim 15, wherein when said engagement member is engaged in said right hand set of threads the shank is able to be inserted into the substrate.

17. The system of claim 12, wherein said engagement section comprises a left hand set of threads formed on the interior of said holding member and adapted to engage a left hand set of threads formed on said engagement member.

18. The system of claim 17, wherein when said engagement member is engaged in said left hand set of threads the shank is able to be removed from the substrate.

19. The system of claim 12, wherein said holding member comprises shank threads formed internally in said first bore, wherein said shank threads are adapted to mate with threads formed on an exterior of the shank.

20. An instrument for inserting and removing a modular screw shank, said instrument comprising:
    a holding member operable to hold the modular screw shank;
    an engagement member movable between an engaged position and a non-engaged position;
    an engagement system adapted to direct said engagement member between said engaged position and said non-engaged position; and
    a countersinking section;
    wherein when said engagement member is in said engaged position the modular screw shank is locked relative said holding member;
    wherein said engagement member includes an insertion engagement member and a removal engagement member;
    wherein said insertion engagement member is used with the holding member to insert the modular screw shank and said removal engagement member is used with said holding member to remove the modular screw shank.

21. The instrument of claim 20, wherein said holding member defines said countersinking section at an end of said holding member.

22. The instrument of claim 21, wherein the countersinking defined by the holding member is near the end of the holding member operable to hold a modular screw shank.

23. An instrument for inserting and removing a modular screw shank, said instrument comprising:
    a holding member operable to hold the modular screw shank;
    an engagement member movable between an engaged position and a non-engaged position; and
    an engagement system adapted to direct said engagement member between said engaged position and said non-engaged position; and
    a countersinking section;
    wherein when said engagement member is in said engaged position the modular screw shank is locked relative said holding member;
    wherein said countersinking section is operable to form an area in a substrate to receive a head operable to interconnect with the modular screw shank.

24. The instrument of claim 23, wherein said holding member comprises:
- a cannulated member having a first end and a second end; and
- a shank engagement system formed in said first end of said cannulated member;
- wherein said engagement system is positioned in said second end of said cannulated member.

25. The instrument of claim 23, wherein said holding member comprises a cannulated member having a first end and a second end;
- a set of shank engaging threads adjacent said first end;
- wherein said engagement member includes longitudinally extending external member threads; and
- wherein said engagement system is a set of engaging threads adapted to substantially mate with said external member threads.

26. The instrument of claim 25, wherein said engagement member is movable between said engaged position and said non-engaged position via said engaging threads.

27. The instrument of claim 20, wherein said holding member defines right hand threads and said insertion engagement member defines right hand threads wherein said engagement system includes the right hand threads of the holding member and the right hand threads of the insertion engagement member to insert the modular screw shank.

28. The instrument of claim 20, wherein said holding member defines left hand threads and said removable engagement member includes left hand threads;
- wherein said engagement system includes the left hand threads of said holding member and the left hand threads of said engagement member to allow for removal of said modular screw shank.

* * * * *